United States Patent
Muniraju

(10) Patent No.: US 10,568,505 B2
(45) Date of Patent: Feb. 25, 2020

(54) WEARABLE DEVICE FOR EYE MOVEMENT DETECTION

(71) Applicant: Nokia Technologies Oy, Espoo (FI)

(72) Inventor: Swetha Muniraju, Burlingame, CA (US)

(73) Assignee: Nokia Technologies Oy, Espoo (FI)

( * ) Notice: Subject to any disclaimer, the term of this patent is extended or adjusted under 35 U.S.C. 154(b) by 0 days.

(21) Appl. No.: 15/840,254

(22) Filed: Dec. 13, 2017

(65) Prior Publication Data

US 2018/0177393 A1 Jun. 28, 2018

(30) Foreign Application Priority Data

Dec. 23, 2016 (EP) .................................. 16206560

(51) Int. Cl.
*A61B 5/103* (2006.01)
*A61B 3/113* (2006.01)
(Continued)

(52) U.S. Cl.
CPC ............ *A61B 3/113* (2013.01); *A61B 5/0496* (2013.01); *A61B 5/1103* (2013.01);
(Continued)

(58) Field of Classification Search
CPC ..... A61B 3/113; A61B 5/1121; A61B 5/1123; A61B 5/4815; A61B 5/7207;
(Continued)

(56) References Cited

U.S. PATENT DOCUMENTS 3,626,514 A * 12/1971 Sacco .................... G02C 11/00
2/12
4,836,219 A    6/1989 Hobson et al.
(Continued)

FOREIGN PATENT DOCUMENTS

WO    1998/043536 A1    10/1998
WO    2006/039346 A1    4/2006

OTHER PUBLICATIONS

"The Drones Controlled by Make-up: Conductive Eyeshadow and False Eyelashes Let Wearers Drive Aircraft by Blinking", Mail Online, Retrieved on Dec. 14, 2017, Webpage available at : http://www.dailymail.co.uk/sciencetech/article-2474788/The-drones-controlled-MAKE-UP-Conductive-eyeshadow-false-eyelashes-let-wearers-drive-aircraft-blinking.html.
(Continued)

*Primary Examiner* — William R Alexander
*Assistant Examiner* — Henry A Duong
(74) *Attorney, Agent, or Firm* — Alston & Bird LLP

(57) ABSTRACT

A method, apparatus and computer program product are provided for detecting eye movement with a wearable device attachable to an eyelid. The wearable device may include an arrangement of sensors, including any combination of piezoelectric sensors, accelerometers, and/or any other type of sensor. An external device may be provided for processing sensor data. The wearable device and/or external device may analyze the sensor data to generate eyeball movement data, and to differentiate first directional data and second directional data. The first directional data may be considered as movement occurring substantially horizontally and the second directional data may be considered as movement occurring substantially vertically. The wearable device and/or external device may therefore provide data regarding sleep cycles of the user.

20 Claims, 12 Drawing Sheets

(51) Int. Cl.
- *A61B 5/0496* (2006.01)
- *A61B 5/11* (2006.01)
- *A61B 5/00* (2006.01)
- *A61F 2/14* (2006.01)

(52) U.S. Cl.
CPC ............ *A61B 5/1114* (2013.01); *A61B 5/1121* (2013.01); *A61B 5/1123* (2013.01); *A61B 5/4812* (2013.01); *A61B 5/4815* (2013.01); *A61B 5/6821* (2013.01); *A61B 5/6832* (2013.01); *A61B 5/7207* (2013.01); *A61B 5/7278* (2013.01); *A61F 2/14* (2013.01); *A61B 5/6898* (2013.01); *A61B 5/721* (2013.01); *A61B 2560/0214* (2013.01); *A61B 2560/0223* (2013.01); *A61B 2560/0475* (2013.01); *A61B 2562/0209* (2013.01); *A61B 2562/0219* (2013.01); *A61B 2562/0261* (2013.01); *A61B 2562/063* (2013.01)

(58) Field of Classification Search
CPC ... A61B 5/7278; A61B 5/4812; A61B 5/6821; A61B 5/1114; A61B 5/1103; A61B 5/0496; A61B 5/6832; A61B 2562/0209; A61B 2562/063; A61B 5/721; A61B 2560/0223; A61B 5/6898; A61B 2560/0214; A61B 2562/0261; A61B 2560/0475; A61B 2562/0219; A61F 2/14; A61F 2009/00846
USPC ........................................................ 351/209
See application file for complete search history.

(56) References Cited

U.S. PATENT DOCUMENTS

| | | | |
|---|---|---|---|
| 2002/0049374 | A1 | 4/2002 | Abreu |
| 2004/0193068 | A1* | 9/2004 | Burton ................. A61B 5/0476 600/544 |
| 2013/0172829 | A1 | 7/2013 | Badawi |
| 2015/0257699 | A1 | 9/2015 | Bjerrum |
| 2016/0097940 | A1 | 4/2016 | Sako et al. |

OTHER PUBLICATIONS

Svensson, "Blink Behaviour Based Drowsiness Detection—Method Development and Validation", Thesis, 2004, 85 pages.
"A Body-Monitoring System With EEG and EOG Sensors", ERCIM News, Retrieved on Dec. 20, 2017, Webpage available at : https://www.ercim.eu/publication/Ercim_News/enw51/bielikova.html.
"High Resolution Detection of Polysomnography Based Phasic Events of Rem Sleep in Postraumatic Stress Disorder", Stanford, Retrieved on Dec. 20, 2017, Webpage available at : https://web.stanford.edu/~hyatt4/content/research/promos/REM%20in%20PTSD%20-%20presentation.pdf.
Uenoyama et al., "Vector-Electro-Oculography and Its Clinical Application. Two-Dimensional Recording of Eye Movements", British Journal of Ophthalmology, vol. 48, Jun. 1964, pp. 318-329.
"Charging Your Smart Contact Lens", Youtube, Retrieved on Dec. 14, 2017, Webpage available at : https://www.youtube.com/watch?v=DFMDN5JR5Yc.
"Sony Patents Contact Lens That Records What You See", CNet, Retrieved on Dec. 14, 2017, Webpage available at : https://www.cnet.com/news/sony-patents-contact-lens-that-records-what-you-see/.
"Intel Mobility at Computex 2014 with Core-M, WiGig, RealSense", Youtube, Retrieved on Dec. 14, 2017, Webpage available at :https://www.youtube.com/watch?v=dNaukc1J_aY&feature=youtu.be.
Malmivuo, "The Electric Signals Originating in the Eye", Bioelectromagnetism: Principles and Applications of Bioelectric and Biomagnetic Fields, Mar. 2012, pp. 1-13.
Bocca et al., "Total Sleep Deprivation Effect on Disengagement of Spatial Attention As Assessed by Saccadic Eye Movements", Clinical Neurophysiology, vol. 117, No. 4, 2006, pp. 894-899.
"Rapid Eye Movement Sleep", Wikipedia, Retrieved on Dec. 14, 2017, Webpage available at : https://en.wikipedia.org/wiki/Rapid_eye_movement_sleep.
"REM Sleep and Saccades", Neuro-Patch, Retrieved on Dec. 14, 2017, Webpage available at : https://dyslectem.info/2015/09/03/rem-sleep-and-saccades/.
Andrillon et al., "Single-Neuron Activity and Eye Movements During Human REM Sleep and Awake Vision", Nature Communications, Aug. 11, 2015, pp. 1-10.
"Experiment: Eye Potentials (The EOG)", Backyard Brains, Retrieved on Dec. 14, 2017, Webpage available at : https://backyardbrains.com/experiments/EOG.
"What is Eye Tracking and How Does It Work?", Imotions, Retrieved on Dec. 14, 2017, Webpage available at : https://imotions.com/blog/eye-tracking-work/.
Eggert, "Eye Movement Recordings: Methods", Neuro-Ophthalmology, vol. 40, 2007, pp. 15-34.
Thomas, "The Dynamics of Small Saccadic Eye Movements", The Journal of Physiology, vol. 200, No. 1, Jan. 1, 1969, pp. 109-127.
Bulling et al., "Eye Movement Analysis for Activity Recognition Using Electrooculography", IEEE Transactions on Pattern Analysis and Machine Intelligence, vol. 33, No. 4, Apr. 2011, pp. 741-753.
Zils et al., "Differential Effects of Sleep Deprivation on Saccadic Eye Movements", Sleep, vol. 28, No. 9, May 2005, pp. 1109-1115.
Extended European Search Report received for corresponding European Patent Application No. 16206560.1, dated Jun. 29, 2017, 9 pages.
Coakley et al., "Minute Eye Movement During Sleep", Electroencephalography and Clinical Neurophysiology, vol. 47, No. 2, Aug. 1979, pp. 126-131.
Itsuki, N. et al., *Characteristics of the EOG Potential Changes Generated by Sacadic Eye Movements of Large Amplitude*, Niihama National College of Technology (1992), 514-518.

* cited by examiner

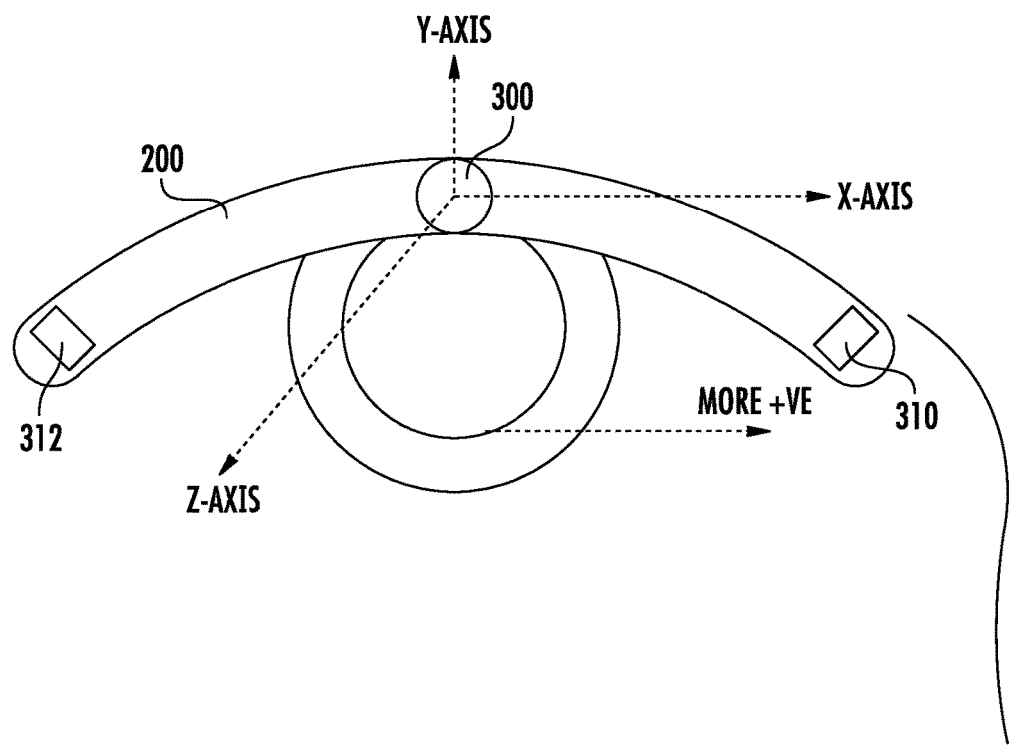
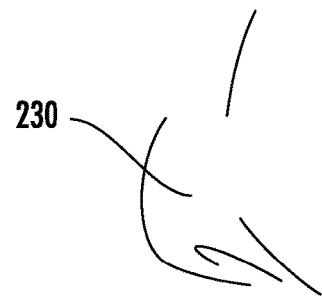
FIG. 3

WEARABLE DEVICE FOR EYE MOVEMENT DETECTION

TECHNOLOGICAL FIELD

An example embodiment of the present disclosure relates generally to eye movement detection, and more particularly, to a method, apparatus and computer program product for detecting eyeball movement with a wearable device attachable to an eyelid.

BACKGROUND

In the area of sleep research and sleep behavior, scientists and medical professionals may monitor eye movements to determine sleep cycles and assess sleep quality. In some studies, electrooculography (EOG) sensors collect and record data relating to the electric charges detected from the eye so that eye movement data can be determined. In some examples, the EOG sensors have been implemented on headbands or nightcaps. In any case, the devices or sensors are often bulky and intrusive to the user while sleeping, and may inhibit the user's movement and/or sleep quality. Additionally, incorrect positioning the EOG sensors on the user's face may result in unreliable or incomplete data.

In some examples, cameras may be used to detect eye movement, but may incur optics limitations and may further require a light source that may disturb a user's sleep. Cameras designed to monitor sleep may require advanced computations and may therefore be costly to implement or purchase. Infrared cameras in sleep tracking may be especially expensive for an individual user to use in everyday life or in their own home.

BRIEF SUMMARY

A method, apparatus, and computer program product are therefore provided for detecting eye movement with a wearable device attachable to an eyelid. The wearable device includes an arrangement of sensors, such as any combination or number of piezoelectric sensors, accelerometers, and/or other type sensors. Certain example embodiments may further include an external device(s) configured to communicate with the wearable device to perform certain operations and functions described herein. The wearable device can be configured to be light weight, communicate wirelessly, and be free of external wires that would in other sleep monitoring devices run obtrusively from the user's face to a nearby machine.

A method is provided, including receiving sensor data from an arrangement of sensors removably attached to an eyelid. The arrangement of the sensors comprises an inner sensor positioned inwards relative to a user's face and an outer sensor positioned outward relative to the user's face and the inner sensor. The method further includes, based on the received sensor data, generating eyeball movement data by differentiating first directional data and second directional data, wherein the first directional data is defined based on an axis associated with the inner sensor and the outer sensor, and the second directional data is defined based on a y-axis substantially orthogonal to the axis associated with the inner sensor and the outer sensor.

In some embodiments, the eyeball movement data comprises movement relative to the y-axis. The method may further include determining whether the first directional data is indicative of a saccadic movement, and preventing second directional data from being attributed to eyeball movement based on the first directional data.

In some embodiments, the inner sensor can be an inner piezoelectric sensor, and the outer sensor can be an outer piezoelectric sensor. The inner piezoelectric sensor and the outer piezoelectric sensors may be configured to detect piezoelectric data. The arrangement of the sensors comprise at least one accelerometer configured to detect acceleration data indicative of movement relative to the y-axis.

The method may include, in an instance a subset of the acceleration data satisfies a head movement threshold, attributing the subset of the acceleration data to head movement. The method also includes in an instance the subset of the acceleration data satisfies a blinking threshold, attributing the subset of acceleration data to blinking. The method can further include, in an instance the subset of the acceleration data is temporally related to the piezoelectric data detected by the inner and outer piezoelectric sensors and the piezoelectric data is indicative of a saccadic movement, attributing the subset of acceleration data to the saccadic movement.

In some embodiments, the arrangement of sensors comprises an array of piezoelectric sensors. In some embodiments, the arrangement of sensors comprises an array of accelerometers. In some embodiments, the arrangement of sensors is comprised by a wearable device removably attached to the eyelid. The eyeball movement data may reflect (a) angular velocity (b) amplitude, and (c) duration.

The method may include determining that the sensor data is associated with a resting potential, and in response to determining that the sensor data is associated with a resting potential, calibrating the sensor data on a memory device.

An apparatus is also provided that is removably attachable to an eyelid, and comprises an arrangement of sensors, at least one processor, and at least one memory comprising computer program code. The at least one memory and the computer program code are configured to, with the processor, cause the apparatus to at least receive sensor data from the arrangement of sensors, and differentiate first directional data and second directional data in the sensor data. The arrangement of sensors may comprise at least two piezoelectric sensors and at least one accelerometer.

In an instance the apparatus is attached to the eyelid, the arrangement of the sensors comprises an inner sensor positioned inwards relative to a user's face and an outer sensor positioned outward relative to the user's face and the inner sensor. The first directional data is defined based on the inner sensor and the outer sensor, and the second directional data is defined based on an upward movement.

A computer program product is provided that comprises at least one non-transitory computer-readable storage medium having computer-executable program code instructions stored therein. The computer-executable program code instructions comprising program code instructions to perform any of the methods described above or hereinafter.

An apparatus is provided, with means for receiving sensor data from an arrangement of sensors removably attached to an eyelid. The arrangement of the sensors comprises an inner sensor positioned inwards relative to a user's face and an outer sensor positioned outward relative to the user's face and the inner sensor. The apparatus further includes, based on the received sensor data, means for generating eyeball movement data by differentiating first directional data and second directional data, wherein the first directional data is defined based on an axis associated with the inner sensor and the outer sensor, and the second directional data is defined based on a y-axis substantially orthogonal to the axis associated with the inner sensor and the outer sensor.

BRIEF DESCRIPTION OF THE DRAWINGS

Figure 1:
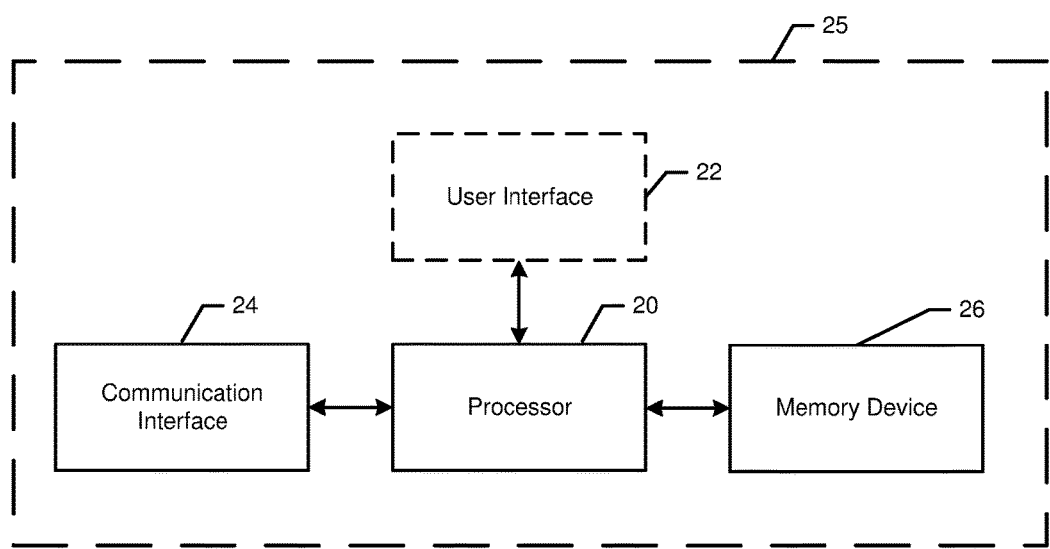
Figure 2:
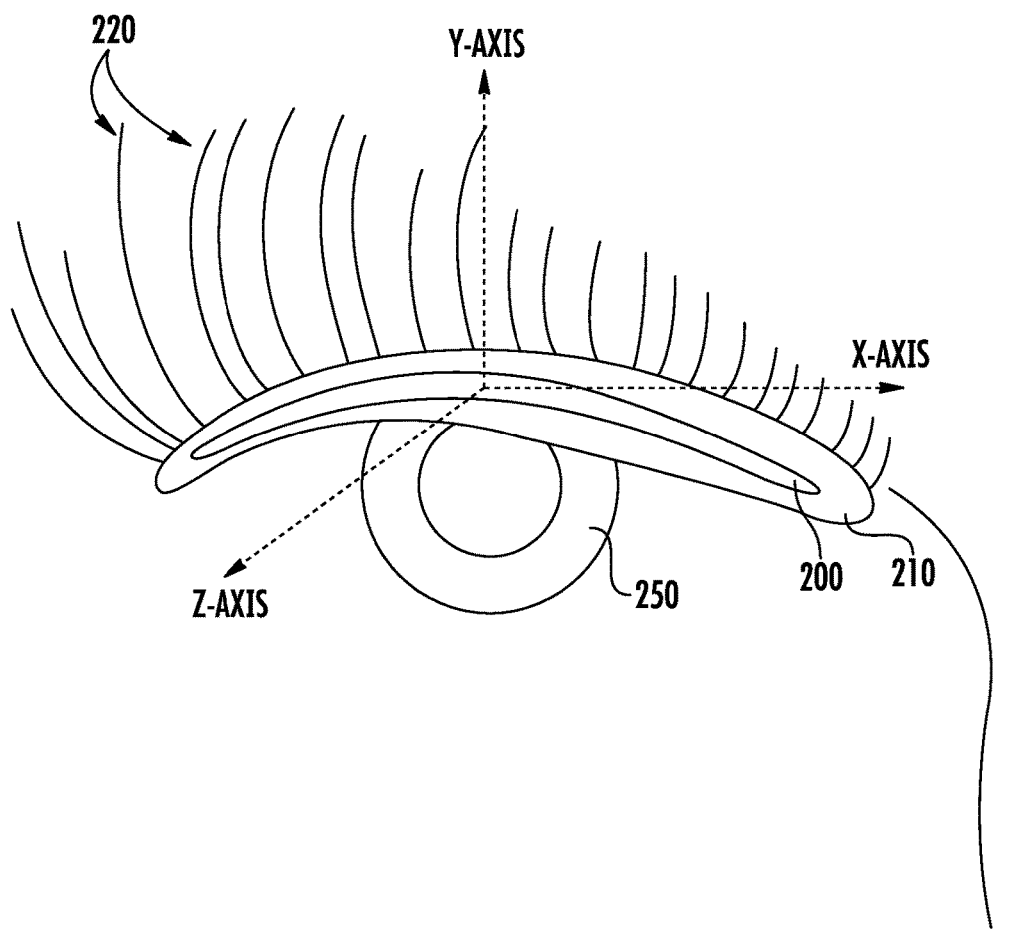
Figure 4:
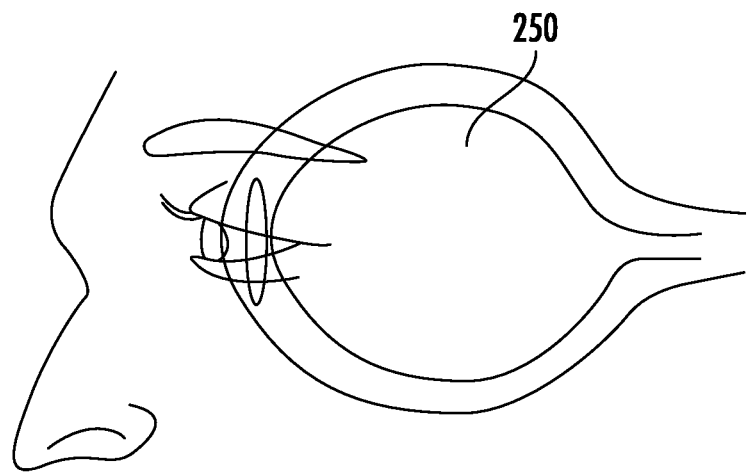
Figure 5:
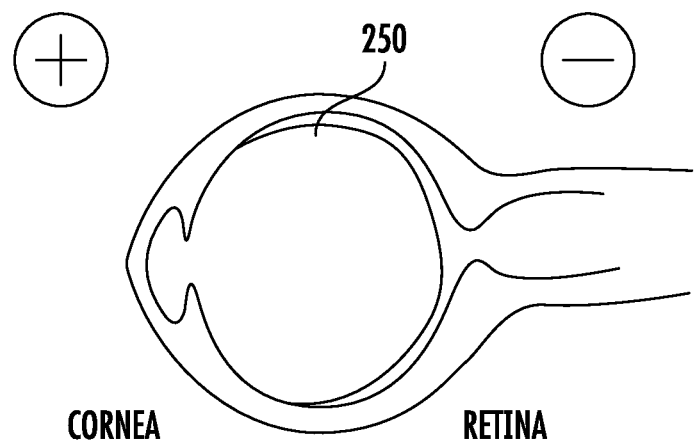
Figure 6:
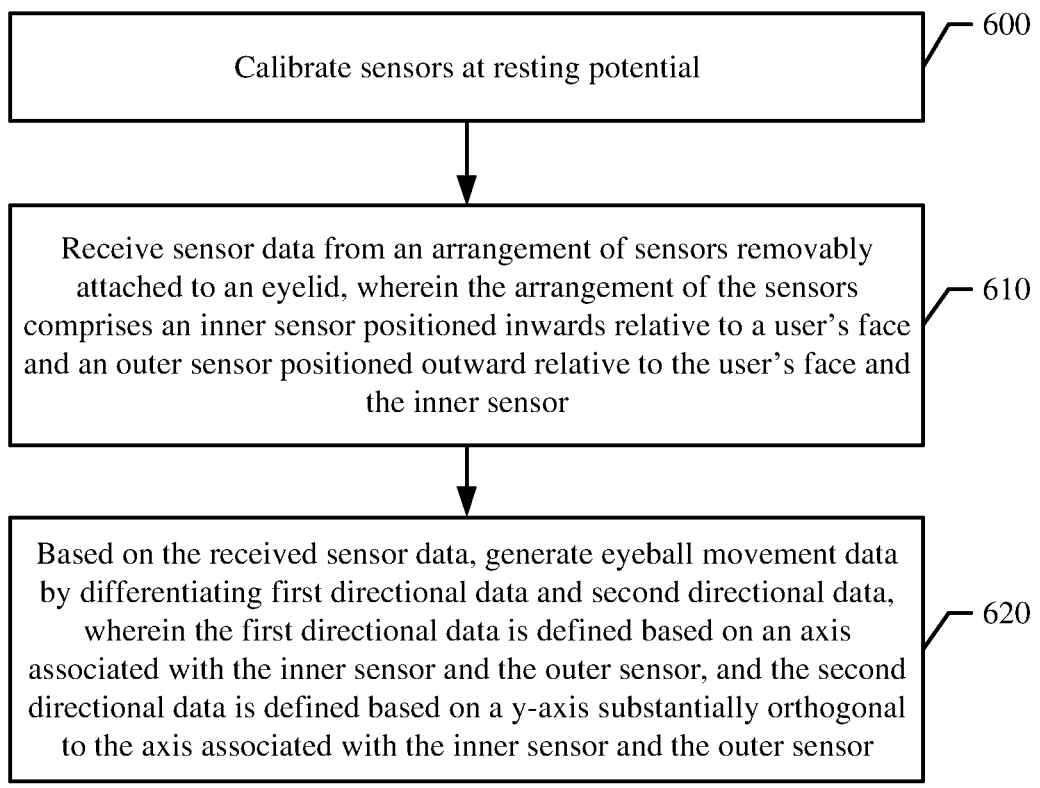
Figure 7:
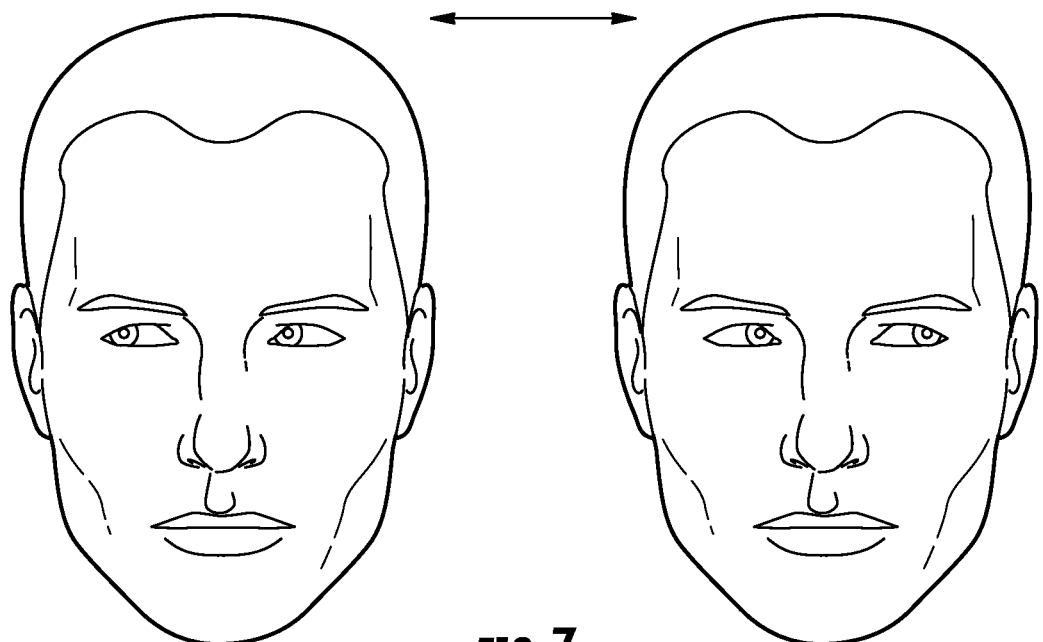
Figure 8:
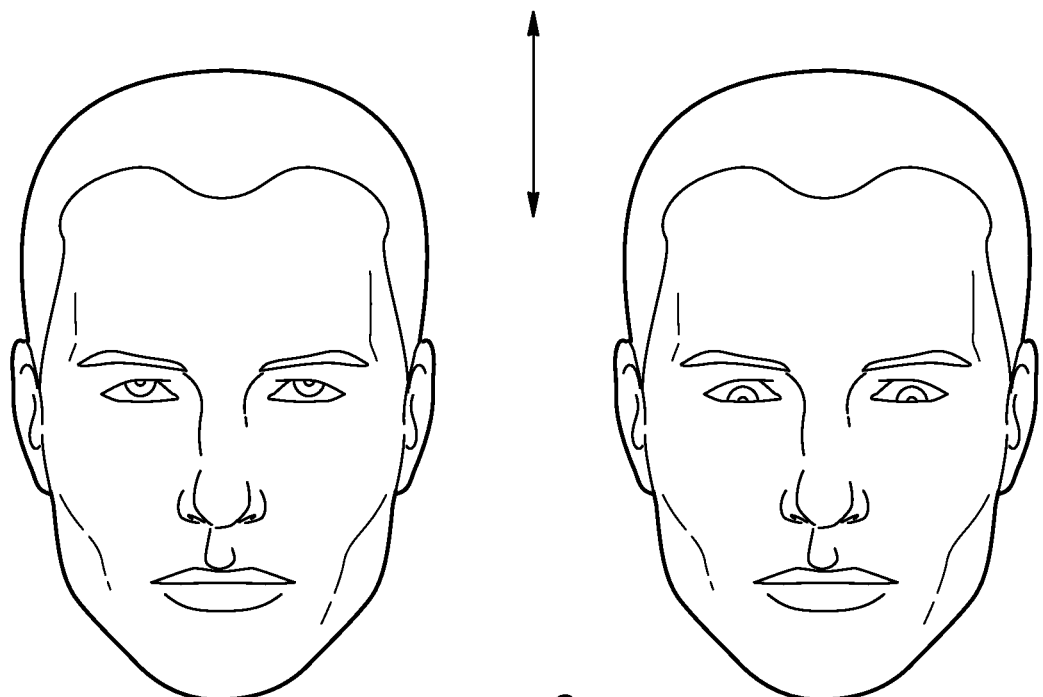
Figure 9:
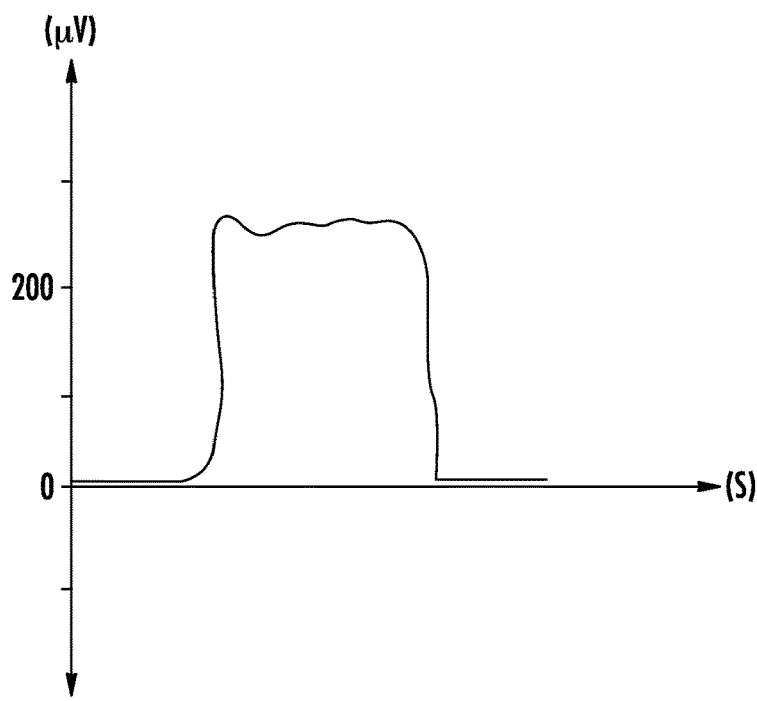
Figure 10:
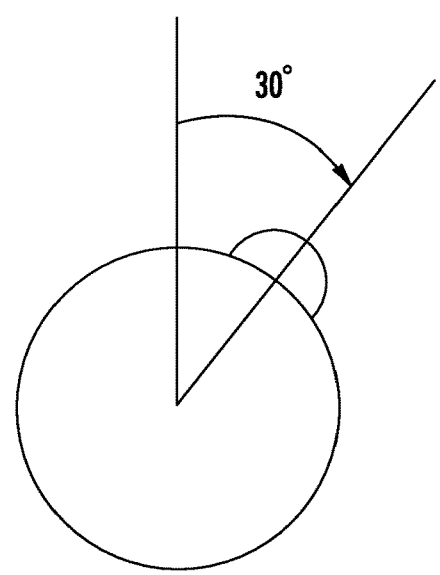
Figure 11:
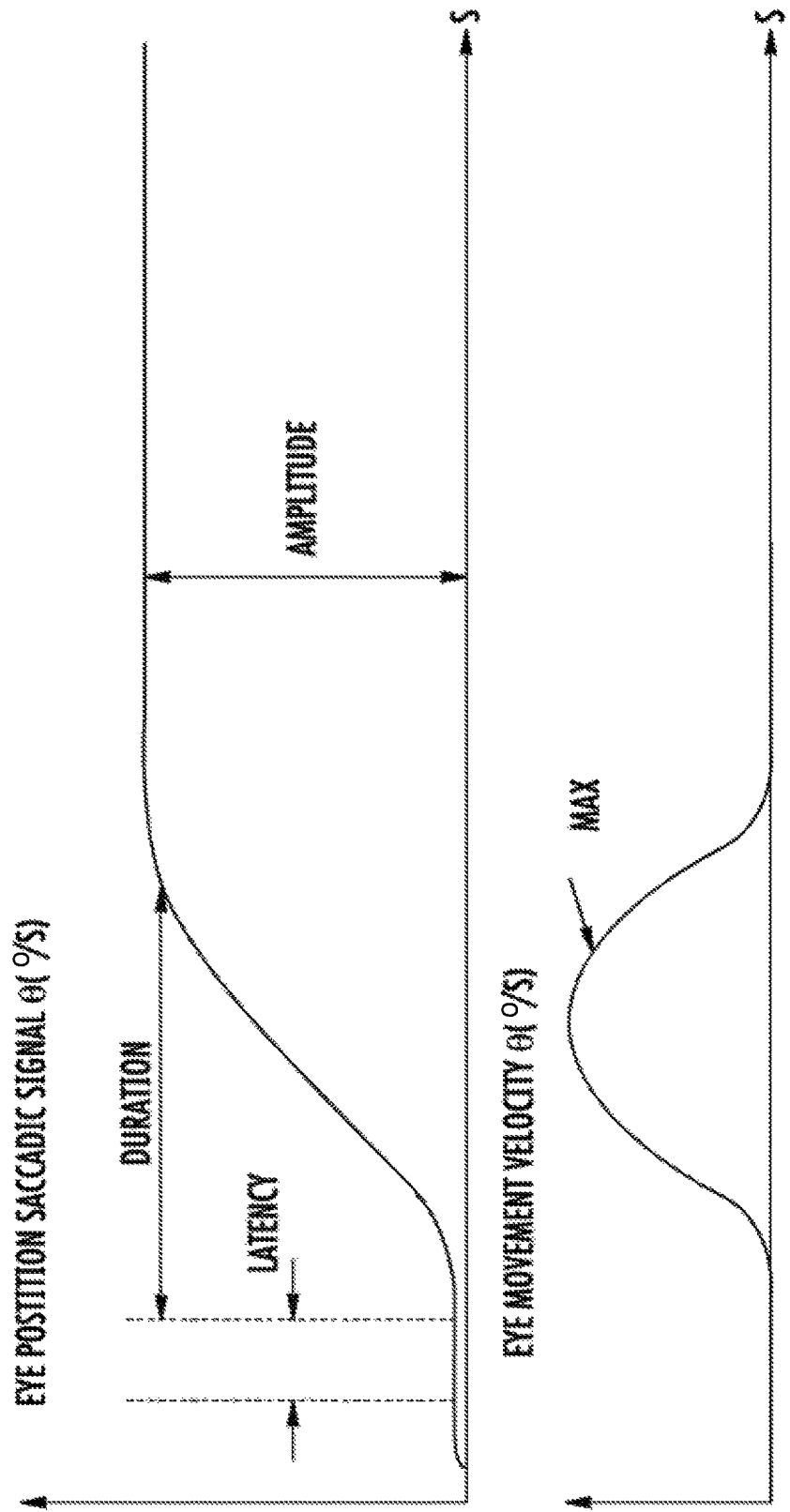
Figure 12:
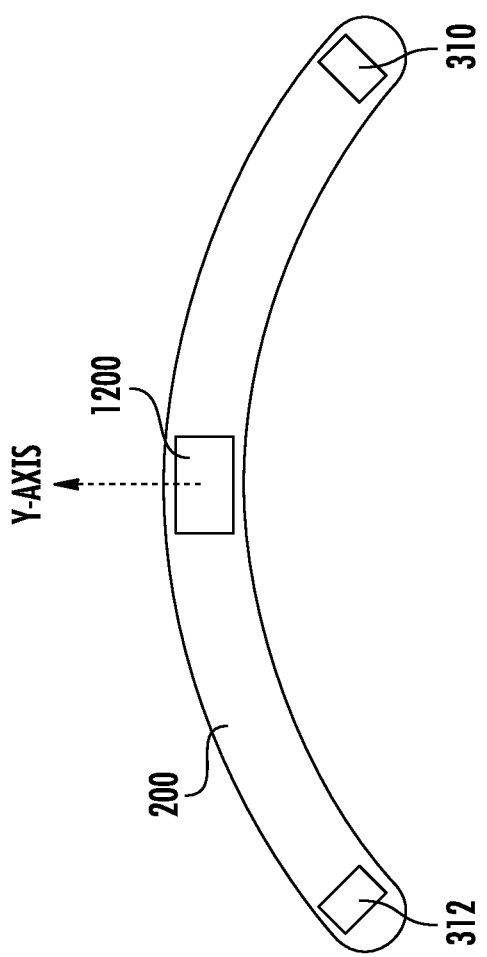
Figure 13:
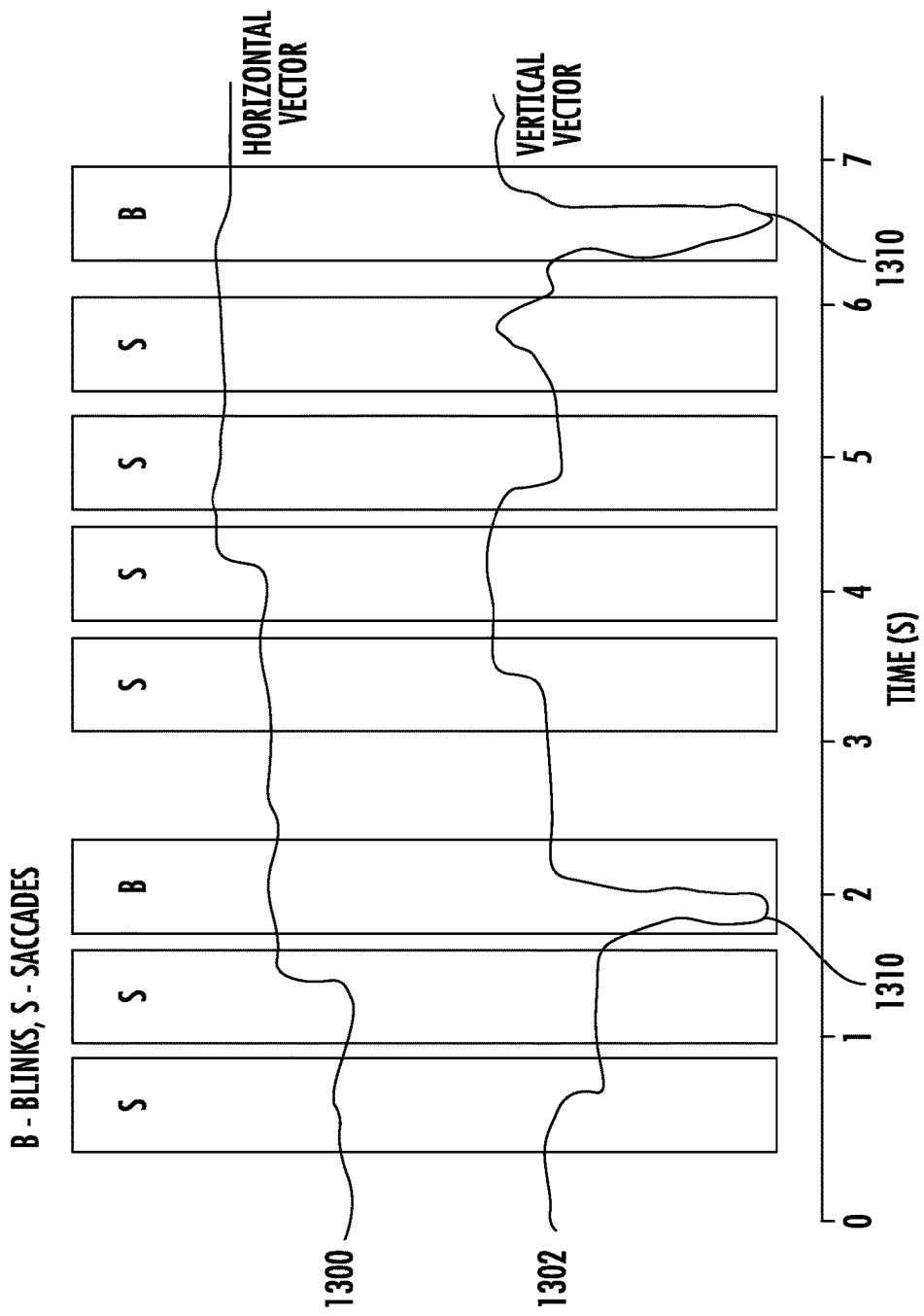
Figure 14:
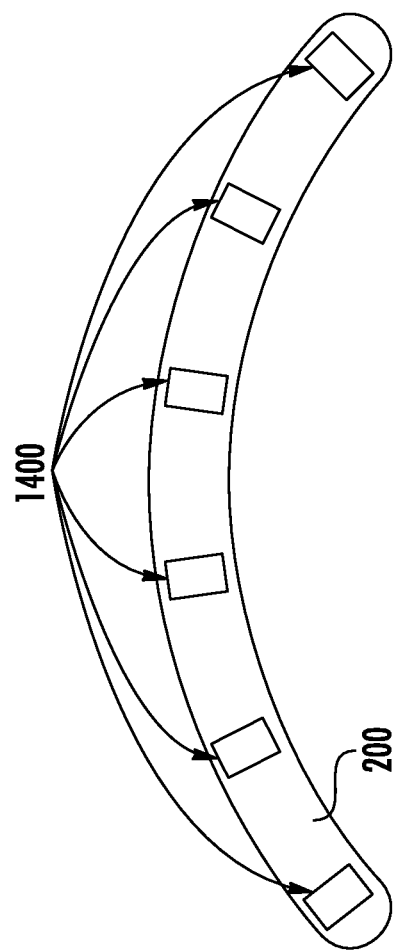
Figure 15:
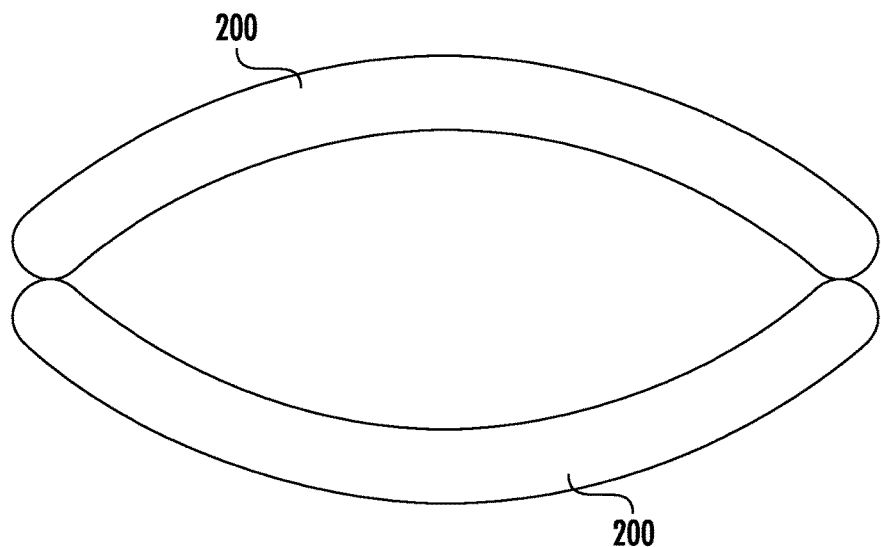
Figure 16:
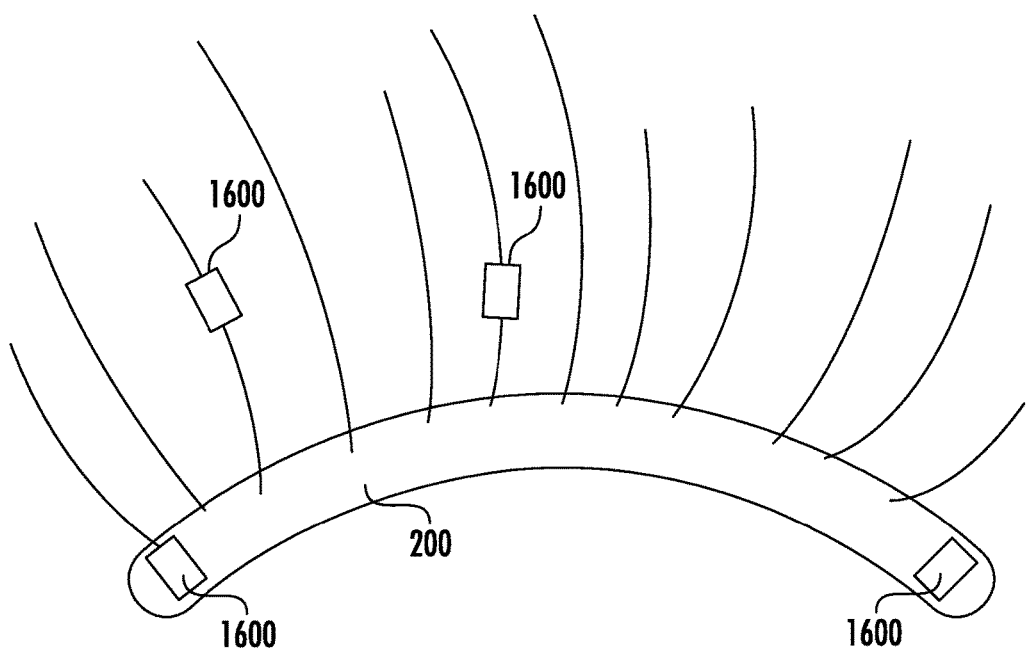

Having thus described certain example embodiments of the present disclosure in general terms, reference will hereinafter be made to the accompanying drawings which are not necessarily drawn to scale, and wherein:

FIG. 1 is a block diagram of an apparatus that may be configured to implement an example embodiment of the present disclosure;

FIG. 2 is a diagram of a wearable device attached to a user's eyelid, in accordance with an example embodiment of the present disclosure;

FIG. 3 is a diagram of a wearable device, in accordance with an example embodiment of the present disclosure;

FIGS. 4 and 5 are diagrams of a user's eye;

FIG. 6 is a flowchart of operations that may be performed, in accordance with an example embodiment of the present disclosure;

FIGS. 7 and 8 are illustrations of substantially horizontal and substantially vertical eyeball movement, in accordance with an example embodiment of the present disclosure;

FIG. 9 provides example sensor data, in accordance with an example embodiment of the present disclosure;

FIG. 10 illustrates example eyeball movement corresponding to the sensor data of FIG. 9, in accordance with an example embodiment of the present disclosure;

FIG. 11 illustrates example eyeball movement data, in accordance with an example embodiment of the present disclosure;

FIG. 12 is a diagram of a wearable device, in accordance with an example embodiment of the present disclosure;

FIG. 13 illustrates example eyeball movement data, in accordance with an example embodiment of the present disclosure; and FIG. 14-16 are diagrams of a wearable device, in accordance with an example embodiment of the present disclosure.

DETAILED DESCRIPTION

Some embodiments of the present disclosure will now be described more fully hereinafter with reference to the accompanying drawings, in which some, but not all, embodiments of the present disclosure are shown. Indeed, various embodiments of the present disclosure may be embodied in many different forms and should not be construed as limited to the embodiments set forth herein; rather, these embodiments are provided so that this disclosure will satisfy applicable legal requirements Like reference numerals refer to like elements throughout. As used herein, the terms "data," "content," "information," and similar terms may be used interchangeably to refer to data capable of being transmitted, received and/or stored in accordance with embodiments of the present disclosure. Thus, use of any such terms should not be taken to limit the spirit and scope of embodiments of the present disclosure.

Additionally, as used herein, the term 'circuitry' refers to (a) hardware-only circuit implementations (e.g., implementations in analog circuitry and/or digital circuitry); (b) combinations of circuits and computer program product(s) comprising software and/or firmware instructions stored on one or more computer readable memories that work together to cause an apparatus to perform one or more functions described herein; and (c) circuits, such as, for example, a microprocessor(s) or a portion of a microprocessor(s), that require software or firmware for operation even if the software or firmware is not physically present. This definition of 'circuitry' applies to all uses of this term herein, including in any claims. As a further example, as used herein, the term 'circuitry' also includes an implementation comprising one or more processors and/or portion(s) thereof and accompanying software and/or firmware. As another example, the term 'circuitry' as used herein also includes, for example, a baseband integrated circuit or applications processor integrated circuit for a mobile phone or a similar integrated circuit in a server, a cellular network device, other network device, field programmable gate array, and/or other computing device.

As defined herein, a "computer-readable storage medium," which refers to a physical storage medium (e.g., volatile or non-volatile memory device), may be differentiated from a "computer-readable transmission medium," which refers to an electromagnetic signal.

As described below, a method, apparatus and computer program product are provided for detecting eye movement with a wearable device attachable to an eyelid. The wearable device, which in many examples, may include one or more wearable components, may include any number of sensors. The sensors may be embedded in an artificial eyelash, for example, and may be removably attached to a user's eye, such as via the eyelid. For example, the device may include an adhesive portion or may be attached to the eyelid with an adhesive material. In some examples, the device may be attached similarly to the manner in which an artificial eyelash attaches to the eyelid. The device may therefore be worn by the user without inhibiting the user's movement's or ability to sleep.

Referring to FIG. 1, apparatus 25 may include or otherwise be in communication with processor 20, communication interface 24, and memory device 26. As described below and as indicated by the dashed lines in FIG. 1, in some embodiments, the apparatus 25 may also optionally include a user interface 22.

Apparatus 25 may be configured as a wearable device 200, described in further detail with respect to FIG. 2 below. In some examples, apparatus 25 may be wholly embodied by the wearable device 200. In some examples, apparatus 25 may include any number of external device(s), such as a computing device implemented externally from the wearable device 200 and configured to receive data from the wearable device 200. In this regard, the external device(s) may process the data as described herein according to an example embodiment.

For example, apparatus 25 may include wearable device 200 that is removably attachable to the eyelid and a first external device, such as a smart phone or personal computer, configured to receive sensor data from the wearable device, such as by near field communication (NFC). In some examples, the first external device may perform processing of the sensor data, and/or may be configured to communicate the sensor data to a second external device, such as a server or distributed system which may process the data according to an example embodiment. It will be appreciated that the wearable device 200 and/or any number of external devices may be included in apparatus 25.

In some examples, apparatus 25 may therefore include, or may otherwise be in communication with a server or distributed system, such as a server for processing sensor data and/or sleep data. In some examples, such as those in which apparatus 25 is implemented as an external device (e.g., external from the wearable device 200), apparatus 25 may include a wide variety of devices including personal computers, work stations, or mobile terminals, such as laptop computers, tablet computers, smartphones or any combination of the aforementioned, and other types of voice and text communications systems. In this regard, an external device embodiment of apparatus 25, may be configured to receive data, such as wirelessly, from wearable device 200 and perform processing of the data on the external device according to the examples provided herein. It will therefore be appreciated that any reference made herein to an external device may include any number or configuration of external devices. For example, the wearable device 200 may transmit data to a mobile device, and the mobile device may transmit data to a server and/or distributed system for further processing. In some cases, the wearable device may be configured to transmit data directly to a server and/or distributed system for further processing. As an example, any of the aforementioned components may be implemented as apparatus 25.

In some embodiments, processor 20(s) (and/or co-processors or any other processing circuitry assisting or otherwise associated with the processor 20) may be in communication with the memory device 26 via a bus for passing information among components of the apparatus 25.

The memory device 26 may include, for example, one or more volatile and/or non-volatile memories. In other words, for example, the memory device 26 may be an electronic storage device (e.g., a computer readable storage medium) comprising gates configured to store data (e.g., bits) that may be retrievable by a machine (e.g., a computing device like the processor 20). The memory device 26 may be configured to store information, data, content, applications, instructions, or the like for enabling the apparatus to carry out various functions in accordance with an example embodiment of the present disclosure. For example, the memory device 26 could be configured to buffer input data for processing by the processor 20. Additionally or alternatively, the memory device 26 could be configured to store instructions for execution by the processor 20. In some embodiments, the memory device 26 may be configured to store sleep data and/or other data collected and/or generated by the apparatus 25.

In some examples, memory 26 may be implemented on the wearable device 200, or partially on the wearable device 200 and partially on a computing device(s). For example, the memory 26 implemented on the wearable device 200 may be small and compact, and configured to store computer program code, that when executed by processor 20 of the wearable device 200, causes transmittal of sensor data from the wearable device 200 (e.g., from the memory device 26) to an external device component of apparatus 25. The memory 26 of an external device may be relatively larger than that of the wearable device 200, and may therefore be more suitable for processing the sensor data as described herein.

In some embodiments, the apparatus 25 may be embodied as a chip or chip set. In other words, the apparatus 25 may comprise one or more physical packages (e.g., chips) including materials, components and/or wires on a structural assembly (e.g., a baseboard). For example, the structural assembly may provide physical strength, conservation of size, and/or limitation of electrical interaction for component circuitry included thereon. The apparatus 25 may therefore, in some cases, be configured to implement an embodiment of the present disclosure on a single chip or as a single "system on a chip." As such, in some cases, a chip or chipset may constitute means for performing one or more operations for providing the functionalities described herein. For example, in instances in which apparatus 25 is embodied by the wearable device 200, processor 20 may comprise a single chip so as to limit the size and weight of the wearable device 200.

However, in some embodiments, the processor 20 may be embodied in a number of different ways. For example, the processor 20 may be embodied as one or more of various hardware processing means such as a coprocessor, a microprocessor, a controller, a digital signal processor (DSP), a processing element with or without an accompanying DSP, or various other processing circuitry including integrated circuits such as, for example, an ASIC (application specific integrated circuit), an FPGA (field programmable gate array), a microcontroller unit (MCU), a hardware accelerator, a special-purpose computer chip, or the like. As such, in some embodiments, the processor 20 may include one or more processing cores configured to perform independently. A multi-core processor may enable multiprocessing within a single physical package. Additionally or alternatively, the processor 20 may include one or more processors configured in tandem via the bus to enable independent execution of instructions, pipelining and/or multithreading.

In an example embodiment, the processor 20 may be configured to execute instructions stored in the memory device 26 or otherwise accessible to the processor 20. Alternatively or additionally, the processor 20 may be configured to execute hard coded functionality. As such, whether configured by hardware or software methods, or by a combination thereof, the processor 20 may represent an entity (e.g., physically embodied in circuitry) capable of performing operations according to an embodiment of the present disclosure while configured accordingly. Thus, for example, when the processor 20 is embodied as an ASIC, FPGA or the like, the processor 20 may be specifically configured hardware for conducting the operations described herein. Alternatively, as another example, when the processor 20 is embodied as an executor of software instructions, the instructions may specifically configure the processor 20 to perform the algorithms and/or operations described herein when the instructions are executed. However, in some cases, the processor 20 may be a processor of a specific device configured to employ an embodiment of the present disclosure by further configuration of the processor 20 by instructions for performing the algorithms and/or operations described herein. The processor 20 may include, among other things, a clock, an arithmetic logic unit (ALU) and logic gates configured to support operation of the processor 20.

Meanwhile, the communication interface 24 may be any means such as a device or circuitry embodied in either hardware or a combination of hardware and software that is configured to receive and/or transmit data from/to a network and/or any other device or module in communication with the apparatus 25. In this regard, the communication interface 24 may include, for example, an antenna (or multiple antennas) and supporting hardware and/or software for enabling communications with a wireless communication network. For example, the communication interface 24 may include an antenna configured to transmit sensor data from the wearable device 200 to an external computing device. Additionally or alternatively, the communication interface 24 may include the circuitry for interacting with the antenna(s) to cause transmission of signals via the antenna(s) or to handle receipt of signals received via the antenna(s). In an example embodiment, communication interface 24 may include a Bluetooth™ low energy (BLE)

interface, and/or a proprietary communication interface for causing transmittal of data from the wearable device 200 to an external device.

In some environments, the communication interface 24 may alternatively or also support wired communication. As such, for example, the communication interface 24 may include a communication modem and/or other hardware/software for supporting communication via cable, digital subscriber line (DSL), universal serial bus (USB) or other mechanisms.

In some embodiments, the apparatus 25 may include a user interface 22 that may, in turn, be in communication with the processor 20 to receive an indication of a user input and/or to cause provision of an audible, visual, mechanical or other output to the user. For example, such as in embodiments in which apparatus 25 includes or is implemented as an external device, user interface 22 may include a keyboard, a mouse, a joystick, a display, a touch screen(s), touch areas, soft keys, a microphone, a speaker, or other input/output mechanisms. Alternatively or additionally, the processor 20 may comprise user interface circuitry configured to control at least some functions of one or more user interface elements such as, for example, a speaker, ringer, microphone, display, and/or the like. The processor 20 and/or user interface circuitry comprising the processor 20 may be configured to control one or more functions of one or more user interface elements through computer program instructions (e.g., software and/or firmware) stored on a memory accessible to the processor 20 (e.g., memory device 26, and/or the like).

FIG. 2 illustrates a wearable device 200 that may embody apparatus 25 or may be included in apparatus 25. In FIG. 2, the wearable device 200 is attached to a user's eyelid 210. Eyelashes 220 are also illustrated in FIG. 2, and may include the user's real eyelashes, or in some examples, may include artificial eyelashes included in the wearable device 200. In FIG. 2, wearable device 200 is illustrated as attached to a top eyelid, but it will be appreciated that the wearable device 200 may be attached to either a top or bottom eyelid, and in some examples, the wearable device 200 may be attached to a top eyelid, and another wearable device 200 may be attached to the bottom eyelid. In this scenario, both the top and bottom eyelid devices may be considered the wearable device 200. Although FIG. 2 depicts a wearable device 200 attached to a user's right eye (note the user's nose 230), the user may have a wearable device(s) 200 attached to one or both eyes.

The x-axis, y-axis, and z-axis are provided in FIG. 2, relative to the user's eye and/or top eyelid, as an example basis for describing positioning of some or all of the components of the wearable device 200 in an instance the wearable device 200 is attached to the user's eyelid. The axes are also referred to as a basis for describing movement of the eyeball. The placement of the axes in FIG. 2 is therefore provided as an example and is not intended to be limiting.

For example, the x-axis may be considered horizontal or substantially horizontal relative to the general shape of the eye. For example, the x-axis may be considered substantially horizontal when the said x-axis is parallel to earth and when the user's body is positioned upright, the user's head and/or neck is straight, not tilted, or tilted only slightly such that the user's head and/or neck appears substantially straight. As depicted in FIG. 2, in some embodiments, the x-axis may intersect the peak of the curvature of the eyelid. For example, the x-axis may intersect the maximum of a curve representative of the upper eyelid, and/or the minimum of a curve representative of the lower eyelid. As another example, in an example embodiment, the x-axis may extend through points of both the inner corner and outer corner of the eye, or one corner of the eye.

The y-axis may therefore be positioned substantially orthogonal or orthogonal to the x-axis. As an example of substantially orthogonal, the y-axis may be within a predefined angular distance from the x-axis, such as 5°. The y-axis may therefore be considered to be positioned vertically or substantially vertically through the center or near-center of the general shape of the eye or length of the user's eyelid (e.g., the center of the line extending between points located coincident with the inner and outer corners of the eye). The y-axis may be orthogonal to earth, when the user's head and/or neck is straight, not tilted, or tilted only slightly such that the user's head and/or neck appears substantially straight. As another example, the y-axis may be positioned over the center of the user's iris when the user's eyeball 250 is focused straight ahead. The y-axis may intersect the peak of the curvature of the eyelid and/or the center of the iris when the user's eye is focused straight ahead.

The z-axis may intersect the x-axis and y-axis at the peak of the curve of the eyelid, and may run outward and inward from the user's eye and/or face, for example. Each of the x-axis, y-axis, and z-axis is perpendicular or orthogonal (or substantially perpendicular or orthogonal) to each other.

The aforementioned description of axes placement is provide relative to the eye, eyelid, and eyeball as a basis for understanding the configuration of the wearable device 200 and the arrangement of sensors comprised therein when the wearable device 200 is attached to the user's eyelid. The aforementioned description is also provided as a basis for describing eyeball movement. However, although the x, y and z-axes are often considered fixed with respect to gravity and/or earth, the descriptions of the x, y, and z-axes are provided herein with respect to the user's eye, eyelid and/or eyeball, and it will be appreciated that the user need not be positioned upright, and the user's head need not be straight for the wearable device 200 to function as described herein. In this regard, the sensors of the wearable device 200 may be calibrated as described in further detail hereinafter, to account for a user's varying positioning, such as lying on the user's back or side, for example, in a bed. The sensors may be further calibrated on an ongoing or repeated basis according to body movements or head movements of the user.

As mentioned above, the wearable device 200 comprises an arrangement of sensors. Various non-limiting example arrangements of sensors are depicted in the example wearable devices 200 of FIGS. 3, 12, and 14-16, and are described in further detail below.

Wearable device 200 may further include hardware components 300, such as a memory 26, processor 20, communication interface 24, and/or a power supply such as a battery. These hardware components may be relatively small, light, and compact so as when wearable device 200 is attached to a user's eyelid, the wearable device 200 is comfortable to wear and not invasive to the user, particularly while sleeping. For example, the battery may include a nano-battery or array thereof and/or may be passively charged. The hardware components 300 are depicted in FIG. 2 as a single component, however, the components may be implemented separately or in any combination. Further, the hardware components 200 may be omitted from other figures to avoid over complicating the drawings, but it will be appreciated that any of the hardware components 300 may be implemented in any of the example configurations of wearable device 200.

The example wearable device 200 of FIG. 3 also includes sensors 310 and 312. Although two sensors are illustrated in FIG. 3, any number of sensors may be present in wearable device 200 and/or apparatus 25. In this example, and in other instances in which the wearable device 200 is configured to be attached to the user's right eye, sensor 310 may be considered an inner sensor positioned inwards relative to a user's face. Sensor 312 may be considered an outer sensor positioned outward relative to the user's face and the inner sensor. Said differently, when the wearable device 200 is attached to a user's eyelid, the sensor 310 may be closer to the user's nose 230 and the sensor 312 may be further from the user's nose. In the illustrated example in which the wearable device 200 is attached to a user's right eye, sensor 310 may be considered the right sensor and sensor 312 may be considered the left sensor.

In this regard, sensors 310 and/or 312 may be configured to be positioned within a threshold distance of the respective inner and outer corners of the eyelids. The corners of the eyelids may be considered as an area where the upper eyelid meets the lower eyelid. For example, sensors 310 and 312 may be positioned within 10 millimeters of the inner and outer corners of the eyelid. In some examples, the wearable device 200 may be configured such that when the wearable device 200 is attached to the user's eyelid, one of the inner or the outer sensor is placed in the corner of the respective eyelid, and due to the varying size of users' eyes and an optionally fixed location of the inner and outer sensors relative to the wearable device 200, the other of the inner or outer sensor may lie substantially close to, or within a threshold distance of the respective corner of the eyelids.

As another example, in an instance in which the wearable device 200 is attached to a user's eyelid, the inner sensor and outer sensor may be positioned on the opposite sides of the y-axis from each other. The inner sensor and/or outer sensor may be positioned a predefined distance from the center of the user's eyelid 210, or a predefined distance from the y-axis. The predefined distances of each respective sensor from a point on the eye may be the same or different from the predefined distance of the other sensor. For example, sensor 310 may be positioned a predefined distance from the center of the user's eye (e.g., different or the same distance as the predefined distance of sensor 312 from the center of eye and/or y-axis), or a predefined distance from the y-axis.

In some examples, the inner and outer sensors may be substantially horizontal relative to each other. An x-axis may therefore run parallel to, substantially parallel to, or through, an axis connecting the inner and outer sensors. As another example, an axis (e.g., line) connecting the inner and outer sensors may be closer to parallel to the x-axis than to the y-axis (and/or z-axis).

The sensors included in the arrangement of sensors in wearable device 200, such as sensors 310 and 312, and other sensors described herein after, may include any type of sensor. For example, piezoelectric sensors and accelerometers are referred to herein as example sensors included in the arrangement. In some examples, any number and/or combination of piezoelectric sensors, accelerometers, and/or other types of sensors may be included in the arrangement of sensors.

The piezoelectric sensors included in the wearable device 200 may be any sensors configured to detect a mechanical stress (e.g., deformation) and convert the detected mechanical stress to a measurable electric potential. The mechanical stress may include a pressure, acceleration, and/or force, for example. In this regard, the piezoelectric sensors may be configured to determine an electric potential of the eyeball based on the mechanical stress and/or deformation applied against the wearable device 200 and detected by the piezoelectric sensor. As referred to herein, piezoelectric data may therefore be considered any data detected by a piezoelectric sensor, such as data indicative of a deformation caused due to a pressure or force caused by eyeball movement and detected by a piezoelectric sensor The electric potential of the eyeball, which may be determined with a piezoelectric sensor, is described in more detail with respect to FIGS. 4 and 5. FIG. 4 is provided so as to provide context of the eyeball 250 relative to the user's head. As illustrated in FIG. 5, the eyeball may be considered a dipole with positive (+ve) pole at the cornea and negative (−ve) pole at the retina, resulting in a higher electric potential when the cornea and/or eyeball is moved away from the y-axis, and a relatively lower electric potential when the cornea and/or eyeball is moved toward or closer to the y-axis. The apparatus 25 is therefore configured to determine varying electric potentials based on the measurable stress detected by a piezoelectric sensor, even while the eye and/or eyelids are closed. In this regard, the electric potential of the eyeball may be referred to as cornea-retina potential.

The electric potential exists irrespective of presence or absence of the light. A resting potential may be defined as the electric potential of an eyeball such that little or no eye movement occurs. In some cases, this resting potential may occur when a user is in a deep sleep, or is still and relaxed. An example resting potential of an eyeball (e.g., resting electric potential) is in the range of 0.4-1.0 mV (millivolts). The resting potential of a particular user may be determined as a baseline such that changes in electric potential, as described hereinafter, can be determined relative to the resting potential. Based on sensor placement on a particular user, the detected resting potential may vary. This variation may be accounted for by calibration of the sensors, described in further detail hereinafter.

As indicated in FIG. 3, a piezoelectric sensor, such as sensor 310, may be positioned such that apparatus 25, such as with processor 20, determines an increase in electric potential as the eyeball 250 moves toward the piezoelectric sensor (illustrated as "more +ve"). The increase in electric potential is determined based on the detected pressure of the eyeball 250 and/or deformation against the skin surface or eyelid. Positioning of the eyeball may therefore be detected, and eyeball movement data generated based on positioning data determined at various time intervals and/or by various sensors. Conversion of the sensor data detected by a piezoelectric sensor to eyeball movement data is described in further detail hereinafter.

In addition to providing electric potential readings, in some examples, a piezoelectric sensor may be configured such that the movement is converted into energy to power the wearable device 200 and/or a battery included in wearable device 200.

In addition to or as an alternative to piezoelectric sensors, any number of accelerometers may be included in the arrangement of sensors in the wearable device 200. An accelerometer may be any sensor configured to detect and/or measure acceleration. The acceleration detected by the accelerometer may include, for example, acceleration caused by movement of the head, eyelid 210, and/or eyeball 250. For example, movement of the eyelid 210 may occur as a result of blinking and should not be attributed to eyeball movement. Movement of the eyeball 250 may be detected by an accelerometer when pressure of the eyeball 250 against the eyelid 210 results in a detectable acceleration. Any accelerometers present in wearable device 200 may be calibrated (such as on memory device 26) based on position of the user, such that the acceleration values described herein are considered relative to the x, y, and z-axes referred to herein.

Referring now to FIG. 6, the operations for detecting eye movement with a wearable device attachable to an eyelid, such as wearable device 200 and/or apparatus 25, are outlined in accordance with an example embodiment. In this regard and as described below, the operations of FIG. 6 may be performed by wearable device 200 and/or apparatus 25. For instance, in examples in which apparatus 25 may be implemented as either or both a wearable device 200 and/or external device, some operations may be performed by the wearable device 200 and some operations may be performed by the external device.

As shown by operation 600, apparatus 25 and/or wearable device 200 may include means, such as processor 20, memory device 26 and/or the like, for calibrating the sensors, such as the arrangement of sensors, at a resting potential, such as during but not limited to non-rapid eye movement (REM) cycles. Sensor data may therefore be collected from any of the sensors, and the values stored at memory 26. Said differently, the sensor and/or wearable device 200 may be calibrated based on the resting potential of the user's eyeball(s). In this regard, apparatus 25 and/or wearable device 200 may include means, such as processor 20, for determining that the sensor data is associated with a resting potential, and in response to determining that the sensor data is associated with a resting potential, calibrating the sensor data on a memory device 26.

In some examples, the calibration is repeated throughout a user's sleep to account for repositioning, and turning. The calibration may be performed to account for tilting and/or positioning of the user's head relative to gravitational forces.

Subsequently received sensor data may then be analyzed in comparison to the calibrated sensor data. It will be appreciated that any reference made herein to analysis of the sensor data and/or generation of the eyeball movement data may be based on calibrated sensors and/or sensor values.

As shown by operation 610, apparatus 25 and/or wearable device 200 may include means, such as processor 20, communication interface 24 and/or the like, for receiving sensor data from an arrangement of sensors removably attached to an eyelid. In some examples, the eyelid may include eyelashes, such that the arrangement of sensors may be removably attached to any of the eyelashes. As described above with respect to FIG. 3, the arrangement of the sensors may include an inner sensor (e.g., sensor 300) positioned inwards relative to a user's face and an outer sensor (e.g., sensor 312) positioned outward relative to the user's face and the inner sensor.

In this regard, sensor data may include any data detected by any of the sensors, or provided as an output by any of the sensors, such as to apparatus 25. For example, sensor data detected by a piezoelectric sensor may include the detected pressure and/or associated electric potential. Sensor data detected by an accelerometer may include acceleration measurements.

As shown by operation 620, apparatus 25 and/or wearable device 200 may include means, such as processor 20, communication interface 24 and/or the like, for, based on the received sensor data, generating eyeball movement data by differentiating first directional data and second directional data, wherein the first directional data is defined based on an axis associated with the inner sensor and the outer sensor (e.g., the x-axis), and the second directional data is defined based on a y-axis substantially orthogonal to the axis associated with the inner sensor and the outer sensor.

In general, apparatus 25 differentiates eyeball movement in the horizontal direction from eyeball movement in the vertical direction. The first directional data may be indicative of eyeball movement in a substantially horizontal direction, and the second directional data may be indicative of eyeball movement in a substantially vertical direction. Any reference or description of horizontal and/or vertical movement is not intended to be limiting, and it will be appreciated that an example embodiment may determine movement of the eyeball in a generally horizontal and/or generally vertical direction as may be reasonably interpreted by one skilled in the art, and relative to the axes described with respect to FIG. 2.

For example, FIG. 7 illustrates a general horizontal movement of the eyeball (e.g., first directional data) and FIG. 8 illustrates a general vertical movement of the eyeball (e.g., second directional data). For illustrative purposes the eyes are open in FIGS. 7 and 8 but it will be appreciated that the detected movement described herein may be performed while the eyes are closed.

The first directional data is defined based on an axis associated with the inner sensor and the outer sensors, such as the example x-axis, and/or an axes parallel or substantially parallel to the x-axis. That is, as described above with respect to FIG. 2, in an instance in which an axis or line connecting the inner and outer sensors is closer to parallel to the x-axis than to the y-axis (and/or z-axis), the inner and outer sensors are substantially horizontal from each other. The first directional data may therefore be defined based on an axis that is substantially horizontal. Accordingly, the first directional data may therefore be indicative of a substantially horizontal eyeball movement, as illustrated in FIG. 7.

The second directional data is defined based on a y-axis substantially orthogonal to the axis associated with the inner sensor and the outer sensor. The second directional data may therefore, according to some embodiments, be characterized with movement in a direction that is closer to parallel to the y-axis than to the x-axis and/or z-axis. In this regard, the second directional data may be indicative of a substantially vertical eyeball movement, as illustrated in FIG. 8.

In general, based on relatively large variations of corneoretinal potential values detected by a sensor, and corresponding sensor horizontal vector values, a peak velocity can be calculated for horizontal movement. For example, consider a horizontal movement towards an inner sensor. The value measured by the inner sensor may be more while the value measured by the outward sensor may be less. But if the horizontal movement is toward the outward sensor then the value measured by outer sensor may be more and the inner sensor may be less. Based on relatively smaller variation of corneo-retinal potential values detected by a sensor, and corresponding sensor vertical vector values, a peak velocity can be calculated for vertical movement. For example, the relatively larger and smaller variations may be distinguished based on a predetermined threshold value. This differentiation of directional data is described in further detail below, and is illustrated in FIG. 13.

In additional to directional data, eyeball movement data may include other variables that may be indicative of eyeball movement, such as but not limited to angular velocity (e.g., angular displacement over time), amplitude (change in distance or angle of the eye), duration, and/or latency. These measurements are described in further detail with respect to FIG. 11 below. Any reference to velocity or peak velocity hereinafter may be respectively considered angular velocity and peak angular velocity.

Additionally or alternatively, the eyeball movement data may include various levels of a hierarchy of data and/or various levels of significance with regard to sleep cycles. For example, directional data and/or measurements of eyeball movement may be determined from the sensor data, and the directional data and/or measurements of eyeball movement may be further processed to determine descriptors or characterizations with respect to time, timeframe, or time period which the corresponding sensor data was detected. For example, a subset of sensor data may be attributed to a rapid eye movement (REM) cycle of sleep, which may be characterized by saccades. The characterizations of saccadic movement and/or REM sleep may be included in the eyeball movement data. During the REM phase of the sleep cycle, the body may be suppressed but the eyes may move under the eye lids. These eye movements resemble the regular rapid movement of the eyes from one fixation to another called saccades. As referred to as herein, the detection of saccades may particularly be considered as detection of REM saccades.

Saccadic movements include quick jumps of the eyeball in either a horizontal or vertical direction and may be characterized based on the same or substantially similar movements in both eyes, occurring at the same time or substantially the same time.

In some examples, the saccadic movements may be accompanied by involuntary blinks or infrequent eyelid movement. An example embodiment may distinguish between saccadic movements and the involuntary blinks and/or infrequent eyelid movement as described herein. For example, saccadic movement may be identified based on any of the aforementioned measurable data (e.g., angular velocity, amplitude, and duration) falling below, at, or above a threshold, and/or within a predetermined range of measurements.

In some examples, the saccadic movement can be determined as occurring when eyeball movement in both of a user's two eyes follow a similar or identical pattern (e.g., the eyeball movement in both eyes follows a pattern of movement such that both eyeballs move from one position to another position relative to their respective axes, or such that the one position and the another position are significantly close to each other in both eyes.

FIG. 9 illustrates detected electric potential associated with the eyeball movement illustrated in FIG. 10. The movement of the eyeball towards the right as shown in the FIG. 10 results in more positive value as measured by the sensor located in the direction of the movement (e.g., the sensor detecting the sensor data associated with the electric potential charted in FIG. 9 is positioned on the wearable device 200 such that the eyeball is moving toward the sensor). The opposite effect may occur when the eyeball moves away from the sensor (e.g., the electric potential may be negative).

In some examples, the difference in electric potential relative to the baseline or calibrated resting potential may be proportional to the sine of the angle of the eyeball movement, such as the angle illustrated in FIG. 10. In this example, the voltage charted in FIG. 9 is indicative of an eyeball movement 30° to the right, and a return of the eyeball to a resting or near-resting position (e.g., relatively nearer to the y-axis), or 0°. It will be appreciated that eyeball movement in the opposite direction to that indicated in FIG. 10 may be represented as a range of 0 to −30°. FIG. 9 therefore provides an example detected electric potential indicative of a horizontal saccade, due to the sudden increase in voltage followed by a subsequent return of the eyeball to resting position.

Based on the sensor voltage changes in FIG. 9, the duration, amplitude, and peak or maximum velocity, may be calculated and/or determined as shown in FIG. 11. The saccadic amplitude may represent a peak change in positioning of the eyeball away from a baseline or resting position for a particular period of time. For example, the amplitude may represent the furthest position of the eyeball away from the resting position. The maximum amplitude may occur at a point in time corresponding to a maximum in the angular velocity, adjusted by the latency. The latency represents a relatively small delay in the actual eye eyeball movement relative to the corresponding detected change in velocity as determined according to changes in eyeball position detected by the sensors and/or arrangement of sensors. For the purpose of sleep studies, the latency may be considered insignificant as it may only represent a delay of several milliseconds in comparison to the study of data spanning several minutes or hours.

The duration may refer to the period of time in which the eyeball moves from the baseline or resting position to a particular position from the baseline or resting position, or threshold distance away from the baseline distance or resting position. In some examples duration may include the duration of a single saccade including the return of the eyeball to the resting position or near-resting position.

In general, or in an average human, the speed, or detectable speed of the human eyeball may range from 20-700°/s. The distance or angular motion of the eye, may be in the range of 0-30°.

Example parameters utilized in the analysis of saccadic performance may include the angular velocity, amplitude and duration. In some examples, latency may be considered, or may be insignificant. When apparatus 25 detects any of the aforementioned measurable parameters falling below, at, or above a threshold, and/or within a predetermined range of measurements, the data may be identified as attributed to saccadic movement.

Example values of these parameters, when determined to be indicative of saccadic movement, may include an angular velocity of 300°/s or more, amplitude of 10° or more, and a duration of 30 ms or more. Latency may be approximately 200 ms but may be considered insignificant in the study of saccadic movements with regard to sleep, as described above. These thresholds and ranges are provided merely as an example, and it will be appreciated that other thresholds and ranges may be applied. For example, these values, ranges and/or thresholds may vary from those of non-human animals, or may vary from user to user, such as depending on eye socket size and shape, and eyeball size and shape.

An example embodiment of apparatus 25 and/or the wearable device 200 may, in some examples, differentiate the first directional data from the second directional data based on any of the aforementioned measurements or parameters. The differentiated data may then be further processed to identify associated characteristics or descriptors of the movement.

In some examples, when a measurement such as amplitude exceeds a predetermined threshold, such as 20°, for example, apparatus 25 may differentiate the associated data as first directional data. In some examples, apparatus 25 may determine the first directional data is indicative of a saccadic movement (e.g., horizontal saccade). In this regard, apparatus 25 may differentiate the first direction data from second directional data. Similarly, for peaks in eye position signal that do not reach or exceed 20°, the data may be indicative of non-saccadic eye movement.

When a pattern, such as a predetermined number of peaks in the eye position signal exceed the predetermined threshold (e.g., amplitude of 20°), the corresponding data may therefore be attributed to REM saccades and/or REM sleep cycles. Single occurrences of peaks, or peaks occurring sporadically, may be attributed to non-REM sleep.

It will be appreciated that saccadic data may be influenced by environmental conditions. For example, saccadic parameters may vary in the presence of light, or based on an amount of light present in the environment of the user. Parameters like saccadic amplitude may be slightly reduced in the dark in comparison to an environment with light. Saccadic peak velocity may increase linearly as a function of saccadic amplitude. This relationship of the effect of light on a user's sleep can be analyzed, and the information can be provided to the user.

While the above description and corresponding FIGS. 9-11 provide examples of first directional data (e.g., horizontal eyeball movement), apparatus 25 may determine second directional data, as provided by additional sensors, which may or may not be implemented on the wearable device 200 (in some examples a sensor may be implemented separately from the wearable device 200). In some examples, the inner and outer sensors may be used by apparatus 25 to determine first directional data, and filter data detected by another device. However, in some examples, an additional sensor may be implemented on the wearable device 200.

For example, as illustrated in FIG. 12, the wearable device 200 may, in some examples, include a sensor 1200. The sensor 1200 may be positioned substantially close to (e.g., within a threshold distance of) or along the y-axis. In some examples, the sensor 1200 may be positioned on or substantially close to the origin and/or intersections of any of the axes. Although one sensor located near the y-axis is illustrated in FIG. 12, it will be appreciated that any number of sensors located near the y-axis may be present on wearable device 200 and/or apparatus 25.

Sensor 1200 may therefore be configured to detect sensor data indicative of movement relative to the y-axis. For example, the sensor data detected by sensor 1200 may be indicative of movement in a direction that is closer to parallel to the y-axis than to the x-axis and/or z-axis. In this regard, the movement may be considered substantially vertical.

In instances in which sensor 1200 is implemented as a piezoelectric sensor, the eyeball movement data may be generated using similar methods as described above. As another example, in an instance sensor 1200 is implemented as an accelerometer, apparatus 25 may generate eyeball movement data based on the detected acceleration data as described below.

In some examples, the acceleration data detected by the accelerometer may be caused by various types of movements. For example, if the acceleration data exceeds and/or satisfies a predetermined threshold, such as 100 mm/s$^2$, the associated data and/or movement may be attributed to a movement (e.g., tossing and/or turning) of the head, such as caused by a user tossing or turning in their sleep. In some examples, the threshold may be satisfied for at least a predetermined amount of time, such as for 0.5 seconds, in order for the associated data to be attributed to head movement. In this regard, in an instance a subset of the acceleration data satisfies a head movement threshold, apparatus 25 may attribute the subset of the acceleration data to head movement. Said differently, the subset of acceleration data may be filtered from the sensor data such that the data is not included, or is prevented from being included in eyeball movement data. In such an example, the apparatus 25 may not be dependent on other devices or sensors placed on the head and configured to detect the head movements that could otherwise skew the eyeball movement data and/or introduce unreliable data.

Similarly, in some examples, in an instance the subset of the acceleration data satisfies a blinking threshold, apparatus 25 may attribute the subset of acceleration data to blinking, and/or exclude the data from being attributed to or caused by eyeball movement. The data may therefore be filtered from the sensor data, or may be excluded from the generated eyeball movement data.

As another example, in an instance the subset of the acceleration data is temporally related to piezoelectric data detected by inner and outer piezoelectric sensors and the piezoelectric data is indicative of a saccadic movement, apparatus 25 may attribute the subset of acceleration data to the saccadic movement. For example, although apparatus 25 may generate eyeball movement data indicative of horizontal saccades as described above with respect to FIGS. 9-11, some additional movement, such as subtle movement detected by the sensor 1200 (e.g., accelerometer), may be detected. In such an example, the apparatus 25 may determine that the measurements indicative of substantially horizontal movement are more significant than the measurements (e.g., acceleration) indicative of substantially vertical movement, and the apparatus 25 may filter the subset of acceleration data as attributable to the horizontal saccadic movement. In this regard, apparatus 25 differentiates first directional data and second directional data.

FIG. 13 illustrates example sensor data 1300 detected by sensors 310 and 312, relative to the example sensor data 1302, such as may be detected by sensor 1300. The sensor data 1300 and 1302 are temporally related as the data was respectively detected by the sensors over the same time periods. The apparatus 25 determines that the substantial dips 1310, or minimums, in the sensor data 1302 are indicative of blinks, as indicated by "B," while the more subtle noise (change in eyeball position) is attributed to saccades, as indicated by "S."

As illustrated in FIG. 13, based on large variation of electric potential (e.g., corneo-retinal potential) values and corresponding sensor horizontal vector values, a peak velocity can be calculated for horizontal saccades. Based on small variation of corneo-retinal potential values and corresponding sensor vertical vector values peak velocity can be calculated for vertical saccades.

Different variations of electric potentials such as the data provided in FIG. 13 can be indicative of different eyeball movements. If the values of corneo-retinal potential are close to the resting potential but the sensor values are high in a third vector corresponding to the z-axis, then the data is attributed to blinks. Peaks in both the horizontal and horizontal vector occurring substantially at the same time may be indicative of oblique, rapid eye movement (REM). Peaks in the horizontal vector while the vertical vector remains relatively constant, may be indicative of horizontal eyeball movement Peaks in the vertical vector while the horizontal vector remains relatively constant may be indicative of vertical, slow eye movements (SEM) during REM. Noise in the vertical and horizontal vectors that reflect inconsistent variations in the vertical and horizontal vectors over time, may be indicative of non-conjugative eye movements, or asynchronous eye movements during REM sleep.

Based on data such as that displayed in FIG. 13, the frequency, timing, and/or timestamps of blinks and/or saccades may be generated and/or stored, for example to memory device 26.

While the above description relates to the example configurations of wearable device 200 provided in FIGS. 3 and 12 and corresponding example data processed by the wearable device 200 and/or apparatus 25, it will be appreciated that any configuration of sensor arrangements may be implemented. Additional arrangements that may be implemented by wearable device 200 are described below with respect to FIGS. 14-16.

In this regard, implementing a wearable device 200 having additional sensors in different positions relative to the axes, provides for additional sensor data. The eyeball movement data may therefore be refined and more accurately portrayed by utilizing sensor data collected from sensors positioned in various locations relative to the axes. Apparatus 25 may therefore generate more precise and/or refined eyeball movement data. In this regard, in some examples, the more sensors that are implemented in the wearable device 200, the more closely the generated eyeball movement data represents the actual eyeball movement data.

For example, the wearable device 200 of FIG. 14 includes an array of sensors 1400. Any number of sensors may be included along the wearable device 200. For example, the sensors may generally follow the outline of the eyelid when the wearable device 200 is attached to the user's eyelid. The array of sensors may therefore be oriented substantially horizontal from each other. For example, an axis or line connecting each sensor to a neighboring sensor of the array of sensors may be closer to parallel to the x-axis than to the y-axis and/or z-axis. The sensor data may therefore be collected by each of the sensors in the array. In this regard, each sensor may detect an increasing pressure as the underlying eyeball moves towards the particular sensor, and a decreasing pressure as the eyeball moves away from the sensor. The electric potential and corresponding eyeball movement data may be generated accordingly as described above. Apparatus 25 may therefore generate more finegrained data and accurate positioning data relative to embodiments with fewer sensors.

FIG. 15 illustrates an upper and lower portion of wearable device 200, which may fit along an upper eyelid and lower eyelid, respectively. As another example, separate wearable devices 200 may be attached to an upper eyelid and lower eyelid. Any arrangement of sensors may be implemented in the wearable device 200, such as to optimize the accuracy of the sensor data and the resultant eyeball movement data.

FIG. 16 illustrates another example embodiment of wearable device 200. Any number of sensors 1600 may be configured in the wearable device 200, including those in the eyelashes (e.g., false eyelashes included in the wearable device 200, and/or affixed to the user's real eyelashes). Sensors may alternatively be positioned higher or lower on the eyelid surface relative to the sensors depicted in FIGS. 3 and/or 15, for example. Including sensors in the eyelashes and/or in different positions on the eyelids may provide for additional sensor data relative to the y-axis, and may therefore enable apparatus 25 to more accurately differentiate first directional data and second directional data.

According to an example embodiment described above, wearable device 20 may include any number of sensors. In this regard, multiple different sensor data may be detected over the same periods of time, thereby being temporally related. In an example embodiment, apparatus 25 may process the temporally related sensor data to filter and/or refine the generated eyeball movement data. In this regard, the apparatus 25 may compare data collected by various sensors for the same respective timeframes, and determine what type of movement (e.g., saccadic, non-saccadic, blinking), to which the data is attributed. In this regard, the data may be accurately represented and various sleep cycles, such as REM and non-REM sleep, may be determined based on patterns of the movements identified in the data. In some examples, when the wearable device 200 is configured with relatively more sensors, apparatus 25 may therefore generate relatively more accurate representations of eyeball movement and therefore relatively more accurate corresponding depictions of sleep cycles.

Certain example embodiments disclosed herein may provide distinct advantages over other eye movement detection devices and methods. Many methods and devices used to scientifically evaluate a person's sleep are performed and/or operative in a laboratory based test called polysomnography (PSG). During PSG, three measures may be used as the basis for defining sleep stages. The three measures may include gross brain activity measured by electroencephalogram (EEG), muscle tone measured by electromyography (EMG), and eye-movement recorded via EOG. EOG may be crucial in differentiating rapid eye movement (REM) sleep stage from the other sleep stages. However, as mentioned herein, EOG is traditionally obtained by placing wired electrodes above and below or left and right of the eye.

Certain example embodiments provided here may therefore provide lighter weight, less intrusive, wearable devices that may be used in sleep tracking, and may not require extensive laboratory equipment. At least some example embodiments therefore solve the problem of using multiple electrodes and wires and thereby reduce constrained movement of the user. Therefore, by using an example embodiment over other methods, sleep quality of the user may be maintained or protected. The collected data may therefore provide a more accurate representation of typical sleep of the user.

Moreover, certain example embodiments provide for a more usable device for in-home sleep monitoring due to the more manageable size of the wearable device. The wearable device provided according to an example embodiment may be implemented with relatively less expensive in comparison to other sleep monitoring devices. Sleep lab tests are generally expensive and since the tests often take place in an unfamiliar environment in the sleep laboratory, actual sleep patterns may differ from the true underlying sleep of the subject. Monitoring the subjects sleep using an in-home based solution over longer periods of time (multiple nights) may be a more effective and inexpensive alternative. Other stand-alone wearable sleep trackers or the non-contact (e.g., radar) based sleep solutions do not include EOG measurements or acceleration data. An example embodiment therefore provides improved accuracy in comparison to other at-home sleep monitoring devices.

Certain example embodiments also provide methods of measuring fatigue by measuring saccadic parameters such as saccadic peak velocity. Several factors such as disease, drugs and alcohol influence saccades as well as other eye movements which can be studied during subject's overnight sleep and can be used to aid in improving his/her sleep quality.

As described above, FIG. 6 illustrates a flowchart of an apparatus 25, method, and computer program product according to an example embodiment of the present disclosure. It will be understood that each block of the flowchart, and combinations of blocks in the flowchart, may be implemented by various means, such as hardware, firmware, processor, circuitry, and/or other devices associated with execution of software including one or more computer program instructions. For example, one or more of the procedures described above may be embodied by computer program instructions. In this regard, the computer program instructions which embody the procedures described above may be stored by a memory device 26 of an apparatus 25 employing an embodiment of the present disclosure and executed by a processor 20 of the apparatus 25. As will be appreciated, any such computer program instructions may be loaded onto a computer or other programmable apparatus (e.g., hardware) to produce a machine, such that the resulting computer or other programmable apparatus implements the functions specified in the flowchart blocks. These computer program instructions may also be stored in a computer-readable memory that may direct a computer or other programmable apparatus to function in a particular manner, such that the instructions stored in the computer-readable memory produce an article of manufacture, the execution of which implements the function specified in the flowchart blocks. The computer program instructions may also be loaded onto a computer or other programmable apparatus to cause a series of operations to be performed on the computer or other programmable apparatus to produce a computer-implemented process such that the instructions which execute on the computer or other programmable apparatus provide operations for implementing the functions specified in the flowchart blocks.

Accordingly, blocks of the flowchart support combinations of means for performing the specified functions and combinations of operations for performing the specified functions for performing the specified functions. It will also be understood that one or more blocks of the flowchart, and combinations of blocks in the flowchart, may be implemented by special purpose hardware-based computer systems which perform the specified functions, or combinations of special purpose hardware and computer instructions.

In some embodiments, certain ones of the operations above may be modified or further amplified. Furthermore, in some embodiments, additional optional operations may be included. Modifications, additions, or amplifications to the operations above may be performed in any order and in any combination.

Many modifications and other embodiments of the present disclosures set forth herein will come to mind to one skilled in the art to which these present disclosures pertain having the benefit of the teachings presented in the foregoing descriptions and the associated drawings. Therefore, it is to be understood that the present disclosures are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

The invention claimed is:

1. A method comprising:
   receiving sensor data from an arrangement of sensors removably attached to an eyelid, wherein the arrangement of the sensors comprises an inner sensor positioned inwards relative to a user's nose and an outer sensor positioned outward relative to the user's nose and the inner sensor, wherein at least two of the sensors are piezoelectric sensors configured to detect electric potential; and
   based on the received sensor data, generating eyeball movement data by differentiating between first directional data and second directional data, wherein the first directional data is defined based on an axis associated with the inner sensor and the outer sensor, and the second directional data is defined based on a y-axis substantially orthogonal to the axis associated with the inner sensor and the outer sensor.

2. The method of claim 1, wherein the eyeball movement data comprises movement relative to the y-axis.

3. The method of claim 1, further comprising:
   determining whether the first directional data is indicative of a saccadic movement; and
   preventing second directional data from being attributed to eyeball movement based on the first directional data.

4. The method of claim 1, wherein:
   the inner sensor comprises an inner piezoelectric sensor,
   the outer sensor comprises an outer piezoelectric sensor,
   the inner piezoelectric sensor and the outer piezoelectric sensors are configured to detect piezoelectric data, and
   the arrangement of the sensors further comprises at least one accelerometer configured to detect acceleration data indicative of movement relative to the y-axis.

5. The method of claim 4, wherein the method further comprises:
   in an instance a subset of the acceleration data satisfies a head movement threshold, attributing the subset of the acceleration data to head movement;
   in an instance the subset of the acceleration data satisfies a blinking threshold, attributing the subset of acceleration data to blinking; and
   in an instance the subset of the acceleration data is temporally related to the piezoelectric data detected by the inner and outer piezoelectric sensors and the piezoelectric data is indicative of a saccadic movement, attributing the subset of acceleration data to the saccadic movement.

6. The method of claim 1, wherein the arrangement of sensors comprises an array of piezoelectric sensors.

7. The method of claim 1, wherein the arrangement of sensors comprises an array of accelerometers.

8. The method according to claim 1, wherein the arrangement of sensors is comprised by wearable device removably attached to the eyelid.

9. The method according to claim 1, wherein the eyeball movement data reflects (a) angular velocity, (b) amplitude, and (c) duration.

10. The method according to claim 1, further comprising:
    determining that the sensor data is associated with a resting potential; and
    in response to determining that the sensor data is associated with a resting potential, calibrating the sensor data on a memory device.

11. The method of claim 1, wherein the eyeball movement data indicates a sleep cycle.

12. An apparatus removably attachable to an eyelid, the apparatus comprising:

an arrangement of sensors, wherein the arrangement of the sensors comprises an inner sensor positioned inwards relative to a user's nose and an outer sensor positioned outward relative to the user's nose and the inner sensor, wherein at least two of the sensors are piezoelectric sensors configured to detect electric potential;

at least one processor, and at least one memory comprising computer program code, wherein the at least one memory and the computer program code are configured to, with the processor, cause the apparatus to at least:
receive sensor data from the arrangement of sensors; and
differentiate between first directional data and second directional data in the sensor data, wherein the first directional data is defined based on an axis associated with the inner sensor and the outer sensor, and the second directional data is defined based on a y-axis substantially orthogonal to the axis associated with the inner sensor and the outer sensor.

13. The apparatus of claim 12, wherein the arrangement of sensors further comprises at least one accelerometer.

14. The apparatus of claim 12, wherein the arrangement of sensors comprises an array of piezoelectric sensors.

15. The apparatus of claim 12, wherein the arrangement of sensors comprises an array of accelerometers.

16. The apparatus of claim 12, wherein the apparatus comprises an artificial eyelash.

17. The apparatus of claim 12, wherein:
the inner sensor comprises an inner piezoelectric sensor,
the outer sensor comprises an outer piezoelectric sensor,
the inner piezoelectric sensor and the outer piezoelectric sensors are configured to detect piezoelectric data, and
the arrangement of the sensors further comprises at least one accelerometer configured to detect acceleration data indicative of movement relative to the y-axis.

18. The apparatus of claim 17, wherein:
in an instance a subset of the acceleration data satisfies a head movement threshold, the computer program code are further configured to, with the processor, cause the apparatus to at least: attribute the subset of the acceleration data to head movement;
in an instance the subset of the acceleration data satisfies a blinking threshold, the computer program code are further configured to, with the processor, cause the apparatus to at least: attribute the subset of acceleration data to blinking; and
in an instance the subset of the acceleration data is temporally related to the piezoelectric data detected by the inner and outer piezoelectric sensors and the piezoelectric data is indicative of a saccadic movement, attributing the subset of acceleration data to the saccadic movement.

19. A computer program product comprising at least one non-transitory computer-readable storage medium having computer-executable program code instructions stored therein, the computer-executable program code instructions comprising program code instructions to:
receive sensor data from an arrangement of sensors removably attached to an eyelid, wherein the arrangement of the sensors comprises an inner sensor positioned inwards relative to a user's nose and an outer sensor positioned outward relative to the user's nose and the inner sensor, wherein at least two of the sensors are piezoelectric sensors configured to detect electric potential; and
based on the received sensor data, generate eyeball movement data by differentiating between first directional data and second directional data, wherein the first directional data is defined based on an axis associated with the inner sensor and the outer sensor, and the second directional data is defined based on a y-axis substantially orthogonal to the axis associated with the inner sensor and the outer sensor.

20. The computer program product of claim 19, wherein the computer-executable program code instructions further comprise program code instructions to cause:
determining whether the first directional data is indicative of a saccadic movement; and
preventing second directional data from being attributed to eyeball movement based on the first directional data.

* * * * *